(12) United States Patent
Bogdan et al.

(10) Patent No.: US 9,150,596 B2
(45) Date of Patent: Oct. 6, 2015

(54) FUNCTIONALIZED UNSATURATED DOUBLE-DECKER DERIVATIVES OF DIVINYLSILSESQUIOXANES

(71) Applicant: ADAM MICKIEWICZ UNIVERSITY, Poznań (PL)

(72) Inventors: Marciniec Bogdan, Swarzdęz (PL); Dudziec Beata, Poznań (PL); Żak Patrycja, Poznań (PL)

(73) Assignee: ADAM MICKIEWICZ UNIVERSITY, Poznań (PL)

( * ) Notice: Subject to any disclaimer, the term of this patent is extended or adjusted under 35 U.S.C. 154(b) by 0 days.

(21) Appl. No.: 14/640,618

(22) Filed: Mar. 6, 2015

(65) Prior Publication Data

US 2015/0252064 A1    Sep. 10, 2015

(30) Foreign Application Priority Data

Mar. 10, 2014    (PL) .......................................... 407444

(51) Int. Cl.
*C07F 7/21*    (2006.01)

(52) U.S. Cl.
CPC ....................................... *C07F 7/21* (2013.01)

(58) Field of Classification Search
USPC ................................................. 556/460, 461
See application file for complete search history.

(56) References Cited

U.S. PATENT DOCUMENTS

| 2004/0249103 A1 | 12/2004 | Morimoto et al. |
| 2005/0009982 A1 | 1/2005 | Inagaki et al. |

FOREIGN PATENT DOCUMENTS

| EP | 1428795 A1 | 6/2004 | |
| EP | 1686133 A2 * | 8/2006 | ................ C07F 7/21 |
| WO | 03/024870 A1 | 3/2003 | |

OTHER PUBLICATIONS

Translation of Polish Patent Application No. 392166 filed Aug. 20, 2010.

Kohri et al; "Synthesis and optoelectronic properties of completely carbazole-substituted double-decker-shaped silsesquioxan;." Chem. Lett., 2010, vol. 39; Oct. 5, 2010; pp. 1162-1163.

Espinas et al; "A Silica-supported double-decker silsesquioxane provides a second skin for the selective generation of bipodal surface organometallic complexes;" Organometallics, 2012, vol. 31; Oct. 23, 2012; pp. 7610-7617.

Seurer et al; "Thermal transitions and reaction kinetics of polyhedral silsesquioxane containing phenylethynylphthalimides;" Macromolecules, 2010, vol. 43; Oct. 19, 2010; pp. 9337-9347.

Hay et al; "A novel linear titanium (IV)-POSS coordination polymer," Macromolecules, 2010, vol. 43; Feb. 9, 2010; pp. 2108-2110.

Wu et al; "Synthesis and characterization of organosoluble aromatic polyimides containing POSS in main chain derived from double-decker-shaped silsesquioxane;" Macromolecules, 2008, vol. 41; Apr. 25, 2008; pp. 3481-3487.

* cited by examiner

*Primary Examiner* — Sudhakar Katakam
*Assistant Examiner* — Pancham Bakshi
(74) *Attorney, Agent, or Firm* — Oliff PLC

(57) ABSTRACT

The subject of the invention are new functionalized unsaturated double-decker derivatives of divinylsilsesquioxanes of the general formula 1. In the formula, $R^1$ are the same and stand for an aryl group containing from 1 to 2 rings, $R^2$ are the same and stand for an alkyl group containing carbon atoms from $C_1$ to $C_2$, substituted or unsubstituted aryl group containing from 1 to 2 rings, $R^3$ are the same and stand for a substituted or unsubstituted aryl group containing from 1 to 2 rings or a group of the formula $—R^4-R^5—$, where $R^4$ stands for an alkyl group containing carbon atoms from $C_1$ to $C_3$, while $R^5$ stands for aryl group containing from 1 to 2 rings.

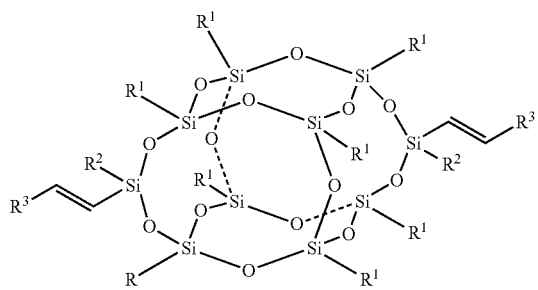

1 Claim, No Drawings

FUNCTIONALIZED UNSATURATED DOUBLE-DECKER DERIVATIVES OF DIVINYLSILSESQUIOXANES

The subject of invention are new functionalized unsaturated double-decker derivatives of divinylsilsesquioxanes.

The structure of double-decker divinyl-substituted silsesquioxanes is different from that of the symmetric system of cubic cages described by the formula $(RSiO_{3/2})_n$, n=8 ($T_8$) and includes two cyclosiloxane rings in parallel planes with 8 inert $R^1$ groups at the silicon atoms of each ring. The rings are joined by bridges of two types: the first type joins the opposite oxygen atoms, while the second type is via $O_2SiCH=CH_2$ groups. In this structure the vinyl groups at the silicon atoms are at the two opposite sides of the molecule and decide about its asymmetry relative to $R^3$ groups at the silicon atoms of siloxane rings (WO2003/024870).

Double-decker functionalized unsaturated derivatives of divinylsilsesquioxanes, built of an inorganic siloxane skeleton that can bind a wide range of functional groups, make suitable substrate for the synthesis of hybrid materials and can be used as nanofillers in the new generation composite materials. The presence of unsaturated carbon-carbon bonds additionally improves the photophysical properties of these compounds. Miyashita has described carbazole silsesquioxane derivatives and their interesting optoelectronic properties that permit their use as organic electroluminescence diodes (M. Kohri, J. Matusi, A. Watanabe, T. Miyashita *Chem. Lett.* 2010, 39, 1162). Lee has presented the use of silsesquioxane derivatives as ligands for the synthesis of titanium coordination compounds that represent the group of metallasilsesquioxane coordination oligomers (M. T. Hay, B. Seurer, D. Holmes, A. Lee *Macromolecules* 2010, 43, 2108), while Basset has reported their use in the synthesis of zirconium and hafnium complexes used as models of catalysts for polymerisation of olefins immobilised on silica (J. Espinas, J. D. A. Pelletier, E. Abou-Hamad, L. Emsley, J.-M. Basset *Organometallics* 2012, 31, 7610). The unsaturated amine and norbornene derivatives of silesquioxanes described by Kakimoto have been used for modification of polyimides; when built in the main polymer chain they considerably improved its thermal and optical properties (S. Wu, T. Hayakawa, M. Kakimoto, H. Oikawa *Macromolecules* 2008, 41).

The known method for the synthesis of double-decker divinylsilsesquioxanes has been presented in patent EP.1428795 and involves the condensation of vinyldichloromethylsilane with a silane derivative of silsesquioxane comprising four reactive Si—OH groups. In this method it is necessary to use chlorosilane susceptible to hydrolysis in the presence of trace amounts of moisture, which interferes with the synthesis and isolation of the product desired. Seurer, B.; Vij, V.; Haddad, T.; Mabry, J. M.; Lee, A. *Macromolecules* 2010, 43, 9337-9347) have revealed the aryl derivatives of silsesquioxanes containing unsaturated bonds, but these bonds are at the external ends of aryl substituents.

Another known method for functionalization of vinylsilsesquioxanes has been revealed in the Polish patent application P. 392166. This method is based on silylative coupling of monovinyl- and octavinyl-substituted silsesquioxanes with olefins in the presence of ruthenium catalyst. The substrates to the above reactions are symmetric silsesquioxane systems ($T_8$, so of the core $Si_8O_8$) with a single reactive vinyl group or with eight vinyl substituents. The silylative coupling reaction leads to mono- or octa-alkenyl substituted products set on a symmetric silsesquioxane core.

The subject of the invention are new functionalized unsaturated double-decker derivatives of divinylsilsesquioxanes, of the general formula 1,

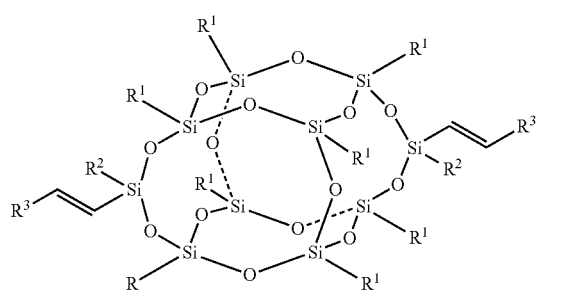

In which
$R^1$ are the same and stand for aryl group containing from 1 to 2 rings,
$R^2$ are the same and stand for:
  Alkyl group from $C_1$ to $C_2$
  Unsubstituted aryl group containing from 1 to 2 rings, or
  Monosubstituted aryl group containing from 1 to 2 rings and substituted at any site of the ring with an alkoxyl group comprising an alkyl group with carbon atoms from $C_1$ to $C_3$,
$R^3$ are the same and stand for
  A group of formula 2

$$-R^4-R^5- \qquad (2)$$

Where $R^4$ stands for an alkyl group comprising carbon atoms from $C_1$ to $C_3$, and $R^5$ stands for an aryl group containing from 1 to 2 rings,
  Unsubstituted aryl group containing from 1 to 2 rings,
  Aryl group containing from 1 to 2 rings and substituted at any site with:
    An alkyl group containing carbon atoms from $C_1$ to $C_2$
    An alkoxyl group comprising an alkyl group containing carbon atoms from $C_1$ to $C_2$
    halogen X=F, Cl, Br
    fully substituted halogenalkyl containing carbon atoms from $C_1$ to $C_2$ and F or Cl The synthesis of functionalized unsaturated double-decker derivatives of divinylsilsesquioxanes of formula 1,

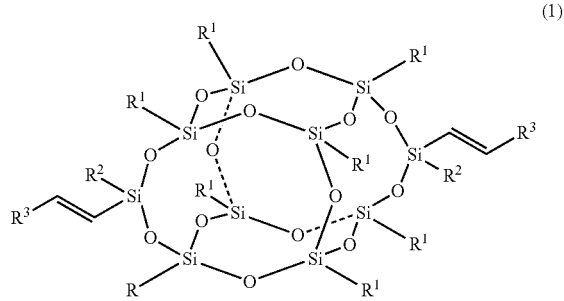

in which $R^1$, $R^2$ and $R^3$ are as defined above, is based on silylative coupling of the double-decker divinylsilsesquioxanes of the general formula 3,

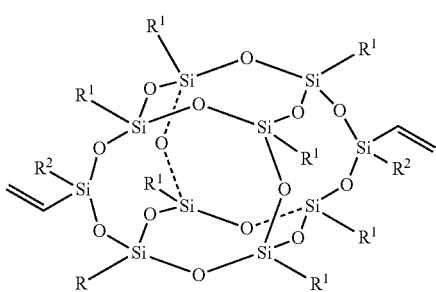

(3)

in which $R^1$ and $R^2$ are as defined above, with olefins of the general formula 4,

4)

in which $R^3$ is as defined above, in the presence of a ruthenium complex as a catalyst. The ruthenium complex used as a catalyst has a general formula 5

$$\text{RuHCl(CO)[P(R}^5)_3]_n \quad (5)$$

In which n stands for 2 or 3; if n=3, then $R^5$ stands for triphenylphosphine, while if n=2, then $R^5$ stands for tricyclohexylphosphine or triisopropylphosphine.

The catalyst is used in the amount from $1\times10^{-3}$ to $1\times10^{-1}$ mole Ru per each mole of the unsaturated group taking part in the reaction of divinylsilsesquioxane of the general formula 3 with an olefin of the general formula 4; it is favourable to use the catalyst in the amount from $0.5\times10^{-2}$ to $2\times10^{-2}$ and the most favourable to use $1\times10^{-2}$ mole. A favourable effect on the course of the reaction has an addition of copper(I) or copper(II) salts as co-catalyst, in particular copper(I) salt, and the most favourable effect has the use of copper(I) chloride in the amount of $10^{-1}$-10 Cu mole, favourably 5 Cu moles per 1 Ru mole.

The reaction is performed in a solvent, under neutral gas atmosphere, in an open or closed system, it is favourable to use gas without oxygen and moisture. In open systems the reaction is performed at a temperature not higher than the boiling point of the reaction mixture. In closed systems the reaction is performed at temperatures not higher than 200° C. It is favourable, but not necessary, to use an excess of olefin with respect to divinylsilsesquioxane to hasten the reaction. It is favourable to use olefin in excess of 1.1 to 2 moles per each mole of $CH_2$=CH groups in divinylsilsesquioxane of formula 3, the most favourable excess of olefin in close to 1.5.

The reaction is performed in a solvent chosen from among: aromatic organic compounds, favourably in toluene, benzene, xylenes, the most favourably in toluene; chlorinated aliphatic compounds or their mixtures. It is favourable to perform the reaction in 1,2-dichloroethane, chloroform, methyl chloride; the most favourable is to use methylene chloride or toluene. It is favourable to perform the reaction in the following way. Proper amounts of divinylsilsesquioxane solvent, alkene and catalyst are placed in a reactor under neutral gas atmosphere. The reaction mixture is stirred upon heating up to 40° C. or higher temperature, and the process is continued at a temperature from 40° C. to the boiling point of the reaction mixture. It is favourable to maintain a constant temperature throughout the process. The reaction takes from 1 to 48 hours.

If a co-catalyst is used, it is introduced to the mixture of reagents and a catalyst after having heated it to a temperature above 40° C. The temperature at which the co-catalyst is introduced must be not lower than 40° C. but not higher than the boiling point of the reaction mixture. The presence of the co-catalyst enhances the rate of the reaction and the yield of the product, and reduces the amount of side products formed. It is favourable to have all the reagents dried and deoxygenated prior to the reaction. The reaction in closed systems is performed in the same conditions and in the open systems.

The raw product is isolated from the reaction mixture by precipitation initiated by a solvent chosen from the groups of aliphatic hydrocarbons containing carbon atoms from $C_5$ to $C_{10}$, MeOH, MeCN, the most favourable is hexane, or by solvent removal. If the second procedure is used, after evaporation of the solvent, the catalyst is washed out by a solvent which is an aliphatic hydrocarbon containing carbon atoms from $C_5$ to $C_{10}$, which selectively dissolves only the catalyst. The raw product can be subjected to further purification on a chromatographic column with the eluent made of a mixture of aliphatic hydrocarbon and a chloroderivative of an aliphatic hydrocarbon; it is favourable to use hexane:methylene chloride at a ratio from the range 10-0:0-10, the most favourably at the ratio 5:5. After purification the eluent is evaporated and pure product is obtained.

The synthesis of double-decker derivatives of divinylsilsesquioxanes according to the invention is illustrated by the examples given below.

The products were analysed by taking the following spectra:

$^1$H and $^{13}$C-NMR on a spectrometer VarianGemini 300, at 300 and 75 MHz $^{29}$Si NMR on a spectrometer VarianAvance 600, at 119 and 203 MHz.

Mass spectra on a 4000 Q TRAP instrument made by Applied Biosystems.

EXAMPLE I

A reactor of 5 mL in capacity, equipped with a magnetic stirrer, reflux condenser and a cap permitting connection of the reaction system to the vacuum-gas line, was charged under argon atmosphere, with 0.1 g of ($8.29\times10^{-5}$ mol) di[9,19-methylvinyl]-1,3,5,7,11,13,15,17 octa(phenyl)pentacyclo[11.7.1.1$^{3,11}$.1$^{5,17}$.1$^{7,15}$]decasiloxane (DDSQ-Me) and then, subsequently with 2 mL of methylene chloride and $17\times10^{-3}$ g ($1.66\times10^{-4}$ mole) styrene. The reaction mixture was heated to 45° C. under continuous stirring. Then, 0.0012 g ($1.66\times10^{-6}$ mole) of carbonylchlorohydridebis(tricyclohexylphosphine)ruthenium(II) was added and after 5 minutes a portion of 0.0008 g ($8.29\times10^{-6}$ mole) of copper(I) chloride was added. The reaction mixture was heated for 18 hours at 45° C. Then, the solvent was evaporated under vacuum and 2 mL of n-hexane was added to wash out the catalyst. After filtration, the precipitate was dissolved in a mixture of hexane:methylene chloride at the volume ratio 1:2 and deposited on a chromatographic column filled with silica in order to remove the traces of catalyst left from the product. The product was obtained in the form of white powder in the yield of 95%.

EXAMPLE II

In the same way as described in example I, a reaction was performed between 0.1 g ($8.29\times10^{-5}$ mole) of divinylsilsesquioxane (DDSQ-Me) and $31\times10^{-3}$ g ($1.66\times10^{-4}$ mole) of 4-bromostyrene, in the presence of 0.0012 g ($1.66\times10^{-6}$

EXAMPLE III

In the same way as described in example I, a reaction was performed between 0.15 g ($1.24 \times 10^{-4}$ mole) of divinylsilsesquioxane (DDSQ-Me) and $35 \times 10^{-3}$ g ($2.49 \times 10^{-4}$ mole) of 4-chlorostyrene in the presence of 0.0018 g ($2.49 \times 10^{-6}$ mole) of carbonylchlorohydridebis(tricyclohexylphosphine)ruthenium(II) and 0.0012 g ($1.24 \times 10^{-5}$ mole) copper(I) chloride. The product was obtained in the form of white powder in the yield of 94%.

EXAMPLE IV

In the same way as described in example I, a reaction was performed between 0.12 g ($9.95 \times 10^{-5}$ mole) of divinylsilsesquioxane (DDSQ-Me) and $27 \times 10^{-3}$ g ($1.99 \times 10^{-4}$ mole) of 4-methoxystyrene in the presence of 0.0014 g ($1.99 \times 10^{-6}$ mole) of carbonylchlorohydridebis(tricyclohexylphosphine)ruthenium(II) and 0.0010 g ($9.95 \times 10^{-6}$ mole) of copper(I) chloride. The product was obtained in the form of white powder in the yield of 91%.

EXAMPLE V

In the same way as in example I, a reaction was performed between 0.1 g ($8.29 \times 10^{-5}$ mole) of divinylsilsesquioxane (DDSQ-Me) and $28 \times 10^{-3}$ g ($1.66 \times 10^{-4}$ mol) of 4-(trifluormethyl)styrene in the presence of 0.0012 g ($1.66 \times 10^{-6}$ mole) of carbonylchlorohydridebis(tricyclohexylphosphine)ruthenium(II) and 0.0008 g ($8.29 \times 10^{-6}$ mole) copper(I) chloride. The product was obtained in the form of white powder in the yield of 90%.

EXAMPLE VI

In the same way as described in example I, a reaction was performed between 0.1 g ($7.52 \times 10^{-5}$ mole) of di[9.19-phenylvinyl]-1,3,5,7,11,13,15,17 octa(phenyl)pentacyclo[11.7.1.1$^{3,11}$.1$^{5,17}$.1$^{7,15}$]decasiloxane (DDSQ-Ph) and $15 \times 10^{-3}$ g ($1.50 \times 10^{-4}$ mole) of styrene in the presence of 0.0011 g ($1.50 \times 10^{-6}$ mole) of carbonylchlorohydridebis(tricyclohexylphosphine)ruthenium(II) and 0.0007 g ($7.52 \times 10^{-6}$ mole) of copper(I) chloride. The product was obtained in the form of white powder in the yield of 903%.

EXAMPLE VII

In the same way as described in example I, a reaction was performed between 0.14 g ($1.05 \times 10^{-4}$ mole) divinylsilsesquioxane (DDSQ-Ph) and $36 \times 10^{-3}$ g ($2.10 \times 10^{-4}$ mole) 4-(trifluormethyl)styrene in the presence of 0.0015 g ($2.10 \times 10^{-6}$ mole) carbonylchlorohydridebis(tricyclohexylphosphine)ruthenium(II) and 0.0010 g ($1.05 \times 10^{-5}$ mole) of copper(I) chloride. The product was obtained in the form of white powder in the yield of 88%.

EXAMPLE VIII

In the same way as described in example I, a reaction was performed between 0.11 g ($8.27 \times 10^{-5}$ mole) of divinylsilsesquioxane (DDSQ-Ph) and $20 \times 10^{-3}$ g ($1.65 \times 10^{-4}$ mole) 4-methylstyrene in the presence of 0.0012 g ($1.65 \times 10^{-6}$ mol) carbonylchlorohydridebis(tricyclohexylphosphine)ruthenium(II) and 0.0008 g ($8.27 \times 10^{-6}$ mole) of copper(I) chloride. The product was obtained in the form of white powder in the yield of 91%.

EXAMPLE IX

In the same way as described in example I, a reaction was performed between 0.1 g ($7.52 \times 10^{-5}$ mole) of divinylsilsesquioxane (DDSQ-Ph) and $28 \times 10^{-3}$ g ($1.50 \times 10^{-4}$ mole) of 4-bromostyrene in the presence of 0.0011 g ($1.50 \times 10^{-6}$ mole) carbonylchlorohydridebis(tricyclohexylphosphine)ruthenium(II) and 0.0007 g ($7.52 \times 10^{-6}$ mole) copper(I) chloride. The product was obtained in the form of white powder in the yield of 95%.

EXAMPLE X

In the same way as described in example I, a reaction was performed between 0.14 g ($1.05 \times 10^{-4}$ mole) of divinylsilsesquioxane (DDSQ-Ph) and $29 \times 10^{-3}$ g ($2.10 \times 10^{-4}$ mol) of 4-chlorostyrene in the presence of 0.0015 g ($2.10 \times 10^{-6}$ mole) carbonylchlorohydridebis(tricyclohexylphosphine)ruthenium(II) and 0.0010 g ($1.05 \times 10^{-5}$ mole) copper(I) chloride. The product was obtained in the form of white powder in the yield of 91%.

EXAMPLE XI

In the same way as described in example I, a reaction was performed between 0.1 g ($7.19 \times 10^{-5}$ mol) di[9,19-(4-methoxyphenyl)vinyl]-1,3,5,7,11,13,15,17 octa(phenyl)pentacylo[11.7.1.1$^{3,11}$.1$^{5,17}$.1$^{7,15}$]deca-siloxane (DDSQ-4-MeOPh) and $14.5 \times 10^{-3}$ g ($1.44 \times 10^{-4}$ mole) styrene in the presence of 0.0010 g ($1.44 \times 10^{-6}$ mole) of carbonylchlorohydridebis(tricyclohexylphosphine)ruthenium(II) and 0.0007 g ($7.19 \times 10^{-6}$ mole) of copper(I) chloride. The product was obtained in the form of white powder in the yield of 87%.

EXAMPLE XII

In the same way as described in example I, a reaction was performed between 0.12 g ($8.63 \times 10^{-5}$ mole) of divinylsilsesquioxane (DDSQ-4-MeOPh) and $31.5 \times 10^{-3}$ g ($1.72 \times 10^{-4}$ mole) of 4-bromostyrene in the presence of 0.0012 g ($1.72 \times 10^{-6}$ mole) of carbonylchlorohydridebis(tricyclohexylphosphine)ruthenium(II) and 0.0008 g ($8.63 \times 10^{-6}$ mole) of copper(I) chloride. The product was obtained in the form of white powder in the yield of 85%.

EXAMPLE XIII

In the same way as described in example I, a reaction was performed between 0.1 g ($7.19 \times 10^{-5}$ mole) of divinylsilsesquioxane (DDSQ-4-MeOPh) and $19.6 \times 10^{-3}$ g ($1.44 \times 10^{-4}$ mole) of 4-chlorostyrene in the presence of 0.0010 g ($1.44 \times 10^{-6}$ mole) carbonylchlorohydridebis(tricyclohexylphosphine)ruthenium(II) and 0.0007 g ($7.19 \times 10^{-6}$ mole) of copper(I) chloride. The product was obtained in the form of white powder in the yield of 90%.

TABLE

Example I

| | |
|---|---|
| Name of compound | Mixture of cis- and trans-di[9,19-(E)-styrylmethyl]-1,3,5,7,11,13,15,17 octa(phenyl)pentacyclo[11.7.1.1$^{3,11}$.1$^{5,17}$.1$^{7,15}$]decasiloxane |
| Formula of compound | 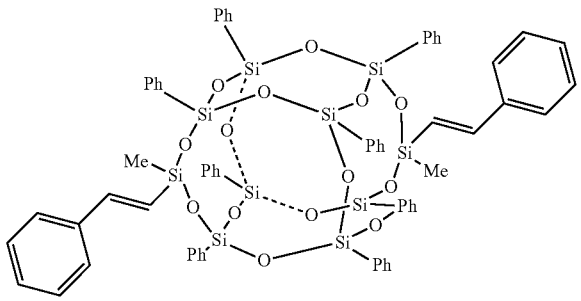 |
| Results of NMR + HRMS analyses | $^1$H NMR (CDCl$_3$, δ, ppm): 0.439-0.445 (overlapping s, 6H, CH$_3$; cis and trans mixture), 6.44 (d, 2H, J$_{HH}$ = 19.3 Hz, =CH—Si), 7.12 (d, 2H, J$_{HH}$ = 19.3 Hz, =CH—C$_6$H$_5$), 6.89-7.6 (m, 50H, C$_6$H$_5$—) <br> $^{13}$C NMR (CDCl$_3$, δ, ppm): −0.79, 123.94, 126.78, 127.52 (t, J = 7.9 Hz), 127.77, 128.38 (d, J = 1.7 Hz), 130.11, 130.21, 130.3, 130.34, 130.54, 130.79, 131.93, 146.59 <br> $^{29}$Si NMR (CDCl$_3$, δ, ppm): −30.17 (cis, trans), −78.30 (cis, trans), −79.15 (cis), −79.51 (trans), −79.84 (cis) <br> HRMS (FD): calcd. for C$_{66}$H$_{60}$O$_{14}$Si$_{10}$Na: 1379.1574; found: 1379.1569 |

Example II

| | |
|---|---|
| Name of compound | Mixture of cis- and trans- di[9,19-(E)-4-bromostyrylmethyl]-1,3,5,7,11,13,15,17 octa(phenyl)pentacyclo[11.7.1.1$^{3,11}$.1$^{5,17}$.1$^{7,15}$] decasiloxane |
| Formula of compound | 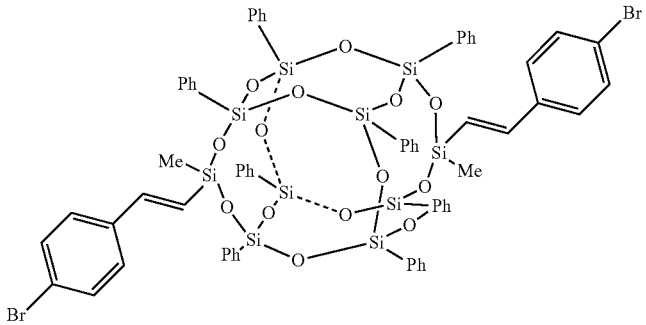 |
| Results of NMR + HRMS analyses | $^1$H NMR (CDCl$_3$, δ, ppm): 0.439-0.445 (overlapping s, 6H, CH$_3$; cis and trans mixture), 6.40 (d, 2H, J$_{HH}$ = 19.3 Hz, =CH—Si), 7.23 (d, 2H, J$_{HH}$ = 19.3 Hz, =CH—C$_6$H$_4$—Br), 6.93-7.58 (m, 48H, C$_6$H$_5$— and C$_6$H$_4$—Br) <br> $^{13}$C NMR (CDCl$_3$, δ, ppm): −0.83, 122.27 (d, J = 1.0 Hz), 124.93, 127.57 (t, J = 5.4 Hz), 127.81, 128.24, 130.39 (d, J = 8.1 Hz), 131.46, 131.78, 133.91, 134.02, 134.05, 136.41, 145.21 <br> $^{29}$Si NMR (CDCl$_3$, δ, ppm): −30.46 (cis, trans), −78.27 (cis, trans), −79.31 (cis), −79.54 (trans), −79.76 (cis) <br> HRMS (FD): calcd. for C$_{66}$H$_{58}$Br$_2$O$_{14}$Si$_{10}$Na: 1534.9784; found: 1534.9783 |

Example III

| | |
|---|---|
| Name of compoud | Mixture of cis- and trans- di[9,19-(E)-4-chlorostyrylmethyl]-1,3,5,7,11,13,15,17 octa(phenyl)pentacyclo[11.7.1.1$^{3,11}$.1$^{5,17}$.1$^{7,15}$] decasiloxane |
| Formula of compound | 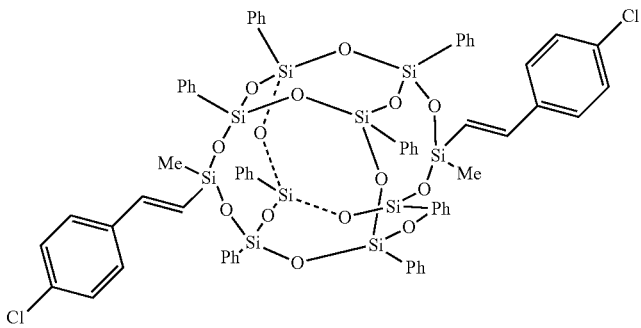 |

| | TABLE-continued |
|---|---|
| Results of NMR + HRMS analyses | $^1$H NMR (CDCl$_3$, δ, ppm): 0.430-0.431 (overlapping s, 6H, CH$_3$, cis and trans mixture), 6.39 (d, 2H, J$_{HH}$ = 19.3 Hz, =CH—Si), 6.92-7.58 (m, 50H, C$_6$H$_5$—, C$_6$H$_4$—Cl and =CH—C$_6$H$_4$—Cl)<br>$^{13}$C NMR (CDCl$_3$, δ, ppm): −0.83, 124.77, 127.57 (t, J = 5.9 Hz), 127.81, 127.94, 128.51, 130.34, 130.42, 130.72, 131.8, 139.92, 134.03, 134.06, 135.99, 145.16<br>$^{29}$Si NMR (CDCl$_3$, δ, ppm): −30.44 (cis, trans), −78.28 (cis, trans), −79.30 (cis), −79.54 (trans), −79.77 (cis)<br>HRMS (FD): calcd. for C$_{66}$H$_{58}$Cl$_2$O$_{14}$Si$_{10}$Na: 1447.0794; found: 1447.0781<br>Example IV |
| Name of compound | Mixture of cis- and trans- di[9,19-(E)-4-methoxystyrylmethyl]-1,3,5,7,11,13,15,17 octa(phenyl)pentacyclo[11.7.1.1$^{3,11}$.1$^{5,17}$.1$^{7,15}$]decasiloxane |
| Formula of compound | (structure shown) |
| Results of NMR + HRMS analyses | $^1$H NMR (CDCl$_3$, δ, ppm): 0.43-0.44 (overlapping s, 6H, CH$_3$, cis and trans mixture), 2.34-2.35 (overlapping s, 6H, —OCH$_3$, cis and trans mixture), 6.38 (br d, 2H, J$_{HH}$ = 19.3 Hz, =CH—Si), 7.09 (br d, 2H, J$_{HH}$ = 19.3 Hz, =CH—C$_6$H$_4$—OMe), 6.91-7.64 (m, 48H, C$_6$H$_5$— and C$_6$H$_4$—OMe)<br>$^{13}$C NMR (CDCl$_3$, δ, ppm): −0.76, 21.26, 122.64, 126.74, 127.52 (t, J = 6.1 Hz), 127.76, 129.08, 130.19, 130.31, 132.01, 133.98, 134.11, 134.9, 138.31, 138.33, 146.55<br>$^{29}$Si NMR (CDCl$_3$, δ, ppm): −29.93 (cis, trans), −78.30 (cis, trans), −79.16 (cis), −79.50 (trans), −79.80 (cis)<br>HRMS (FD): calcd. for C$_{68}$H$_{64}$O$_{16}$Si$_{10}$Na: 1439.1785; found: 1439.1787<br>Example V |
| Name of compound | Mixture of cis- and trans-di[9,19-(E)-4-(trifluoromethyl)styrylmethyl]-1,3,5,7,11,13,15,17 octa(phenyl)pentacyclo[11.7.1.1$^{3,11}$.1$^{5,17}$.1$^{7,15}$]decasiloxane |
| Formula of compound | (structure shown) |
| Results of NMR + HRMS analyses | $^1$H NMR (CDCl$_3$, δ, ppm): 0.46-0.47 (overlapping s, 6H, CH$_3$, cis and trans mixture), 6.52 (br d, 2H, J$_{HH}$ = 19.3 Hz, =CH—Si), 7.11 (br d, 2H, J$_{HH}$ = 19.3 Hz, =CH—C$_6$H$_4$—CF$_3$), 6.91-7.62 (m, 48H, C$_6$H$_5$— and C$_6$H$_4$—CF$_3$)<br>$^{13}$C NMR (CDCl$_3$, δ, ppm): −0.83, 123.03 (d, J = 1.7 Hz), 125.31 (q, CF$_3$), 126.86, 126.87, 127.29, 127.59 (t, J = 9.5 Hz), 127.87, 130.42, 130.51, 130.67, 130.85, 131.73, 133.93, 134.01, 134.05, 134.08, 140.81 (d, J = 1.1 Hz), 144.95<br>$^{29}$Si NMR (CDCl$_3$, δ, ppm): −36.00 (cis, trans), −83.42 (cis, trans), −84.54 (cis), −84.73 (trans), −84.88 (cis)<br>HRMS (FD): calcd. for C$_{68}$H$_{58}$F$_6$O$_{14}$Si$_{10}$Na: 1515.1321; found: 1515.1322<br>Example VI |
| Name of compound | Mixture of cis- and trans- di[9,19-(E)-styrylphenyl]-1,3,5,7,11,13,15,17 octa(phenyl)pentacyclo[11.7.1.1$^{3,11}$.1$^{5,17}$.1$^{7,15}$] decasiloxane |

| Formula of compound | 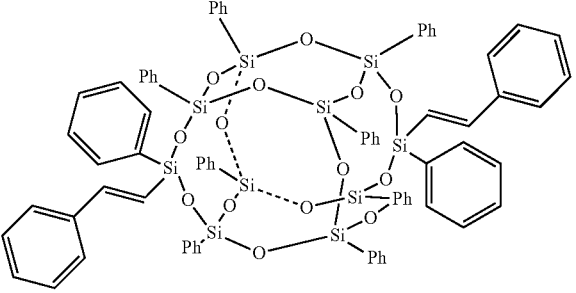 |
|---|---|
| Results of NMR + HRMS analyses | $^1$H NMR (CDCl$_3$, δ, ppm): 6.56 (d, 2H, J$_{HH}$ = 19.2 Hz, =CH—Si, cis and trans mixture), 7.13 (d, 2H, J$_{HH}$ = 19.2 Hz, =CH—C$_6$H$_5$), 6.94-7.75 (m, 60H, C$_6$H$_5$—) <br> $^{13}$C NMR (CDCl$_3$, δ, ppm): 122.26, 126.9, 127.44 (t, J = 7.6 Hz), 127.8, 128.37, 128.53, 130.15 (d, J = 6.1 Hz), 130.41, 130.52, 131.65, 134.01, 134.07, 134.1, 134.54, 137.37, 148.07 <br> $^{29}$Si NMR (CDCl$_3$, δ, ppm): −45.07 (cis, trans), −77.97 (cis, trans), −79.24 (cis), −79.36 (trans), −78.48 (cis) <br> HRMS (FD): calcd. for C$_{76}$H$_{64}$O$_{14}$Si$_{10}$Na: 1503.1887; found: 1503.1874 |

Example VII

| Name of compound | Mixture of cis- and trans- di[9,19-(E)-4-(trifluoromethyl)styrylphenyl]-1,3,5,7,11,13,15,17 octa(phenyl)pentacyclo [11.7.1.1$^{3,11}$.1$^{5,17}$.1$^{7,15}$] decasiloxane |
|---|---|
| Formula of compound | 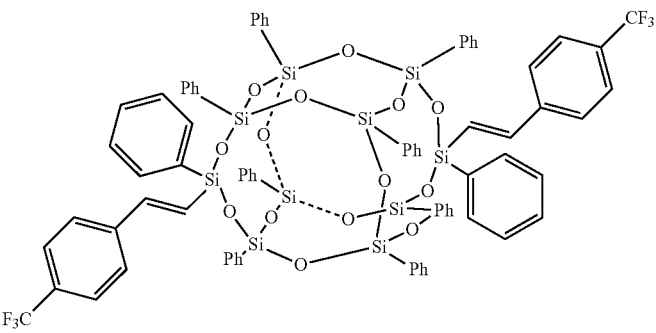 |
| Results of NMR + HRMS analyses | $^1$H NMR (CDCl$_3$, δ, ppm): 6.63 (d, 2H, J$_{HH}$ = 19.2 Hz, =CH—Si), 7.12 (d, 2H, J$_{HH}$ = 19.2 Hz, =CH—C$_6$H$_4$—CF$_3$), 6.97-7.75 (m, 58H, C$_6$H$_5$— and C$_6$H$_4$—CF$_3$) <br> $^{13}$C NMR (CDCl$_3$, δ, ppm): 125.16, 125.25, 125.32 (q, CF$_3$), 125.78 (d, J = 2.0 Hz), 126.98, 127.52 (t, J = 9.7 Hz), 127.89, 127.95, 130.28, 130.34, 130.39, 130.42, 130.5, 130.57, 131.46, 134.03 (d, J = 9.8 Hz), 140.67, 146.31 <br> $^{29}$Si NMR (CDCl$_3$, δ, ppm): −45.21 (cis, trans), −77.87 (cis, trans), −79.35 (cis), −79.40 (trans), −79.42 (cis) <br> HRMS (FD): calcd. for C$_{78}$H$_{62}$F$_6$O$_{14}$Si$_{10}$Na: 1639.1634; found: 1639.1635 |

Example VIII

| Name of compound | Mixture of cis- and trans- di[9,19-(E)-4-methylstyrylphenyl]-1,3,5,7,11,13,15,17 octa(phenyl)pentacyclo[11.7.1.1$^{3,11}$.1$^{5,17}$.1$^{7,15}$] decasiloxane |
|---|---|
| Formula of compound | 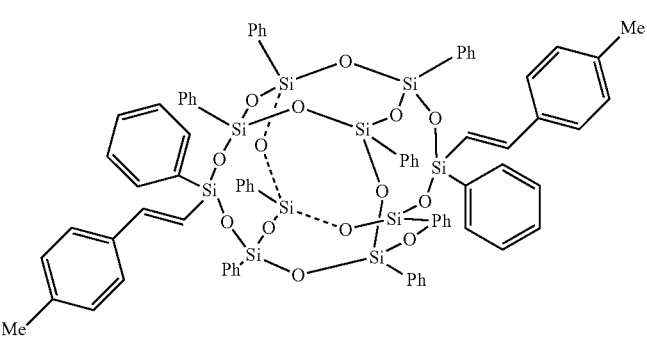 |
| Results of NMR + HRMS analyses | $^1$H NMR (CDCl$_3$, δ, ppm): 2.34 (br s, 6H, CH$_3$, cis and trans mixture), 6.51 (d, 2H, J$_{HH}$ = 19.2 Hz, =CH—Si), 7.11 (d, 2H, J$_{HH}$ = 19.2 Hz, =CH—C$_6$H$_4$—Me), 6.99-7.74 (m, 58H, C$_6$H$_5$— and C$_6$H$_4$—Me) <br> $^{13}$C NMR (CDCl$_3$, δ, ppm): 120.94, 126.87, 127.45 (t, J = 9.6 Hz), 127.79, 129.08, 130.06, 130.16, 130.38, 130.62 (t, J = 5.7 Hz), 131.75, 134.05, 134.14 (t, J = 4.5 Hz), 134.75, 134.8 (d, J = 1.6 Hz), 138.51, 148.07 |

TABLE-continued $^{29}$Si NMR (CDCl$_3$, δ, ppm): −49.46 (cis, trans), −83.21 (cis, trans), −84.49 (cis), −84.57 (trans), −84.66 (cis)

HRMS (FD): calcd. for C$_{78}$H$_{68}$O$_{14}$Si$_{10}$Na: 1531.2199; found: 1531.2198

Example IX

Name of compound: trans-di [9,19-(E)-4-bromo styrylphenyl]-1,3,5,7,11,13,15,17 octa(phenyl)pentacyclo[11.7.1.1$^{3,11}$.1$^{5,17}$.1$^{7,15}$]decasiloxane

Formula of compound:

Results of NMR + HRMS analyses:

$^1$H NMR (CDCl$_3$, δ, ppm): 6.43 (d, 2H, J$_{HH}$ = 19.2 Hz, =CH—Si), 6.96 (d, 2H, J$_{HH}$ = 19.2 Hz, =CH—C$_6$H$_4$—Br), 6.9-7.66 (m, 58H, C$_6$H$_5$— and C$_6$H$_4$—Br)

$^{13}$C NMR (CDCl$_3$, δ, ppm): 122.46 (d, J = 3.1 Hz), 123.4, 127.5 (t, J = 12.2 Hz), 127.85, 127.89, 128.36, 130.26, 130.33, 130.48, 130.5, 131.47 (d, J = 2.2 Hz), 131.54, 133.99, 134.07 (d, J = 2.4 Hz), 136.33 (d, J = 0.9 Hz), 146.64

$^{29}$Si NMR (CDCl$_3$, δ, ppm): −50.02(cis, trans), −83.12 (cis, trans), −84.58 (cis), −84.59 (trans), −84.61 (cis)

HRMS (FD): calcd. for C$_{76}$H$_{62}$Br$_2$O$_{14}$Si$_{10}$Na: 1659.0097; found: 1659.0099

Example X

Name of compound: Mixture of cis- and trans- di[9,19-(E)-4-chlorostyrylphenyl]-1,3,5,7,11,13,15,17 octa(phenyl)pentacyclo[11.7.1.1$^{3,11}$.1$_{5,17}$.1$_{7,15}$]decasiloxane

Formula of compound:

Results of NMR + HRMS analyses:

$^1$H NMR (CDCl$_3$, δ, ppm): 6.51 (d, 2H, J$_{HH}$ = 19.2 Hz, =CH—Si), 7.07 (d, 2H, J$_{HH}$ = 19.2 Hz, =CH—C$_6$H$_4$—Cl), 6.99-7.75 (m, 58H, C$_6$H$_5$— and C$_6$H$_4$—Cl)

$^{13}$C NMR (CDCl$_3$, δ, ppm): 123.2, 127.48 (t, J = 9.3 Hz), 127.82, 127.86, 128.05, 128.49 (d, J = 1.4 Hz), 130.22, 130.29, 130.47, 131.53, 133.97, 134.05 (d, J = 1.9 Hz), 135.88, 146.72

$^{29}$Si NMR (CDCl$_3$, δ, ppm): −44.81(cis, trans), −77.93 (cis, trans), −79.38 (cis), −79.40 (trans), −79.48 (cis)

HRMS (FD): calcd. for C$_{76}$H$_{62}$Cl$_2$O$_{14}$Si$_{10}$Na: 1571.1107; found: 1571.1107

Example XI

Name of compound: Mixture of cis- and trans-di[9,19-(E)-styryl-4-methoxyphenyl]-1,3,5,7,11,13,15,17 octa(phenyl)pentacyclo [11.7.1.1$^{3,11}$.1$^{5,17}$.1$^{7,15}$] decasiloxane

Formula of compound:

| | |
|---|---|
| Results of NMR + HRMS analyses | $^1$H NMR (CDCl$_3$, δ, ppm): 3.79 (br s, 6H, OCH$_3$, cis and trans mixture), 6.58 (d, 2H, $J_{HH}$ = 19.2 Hz, =CH—Si), 7.26 (d, 2H, $J_{HH}$ = 19.2 Hz, =CH—C$_6$H$_5$), 6.81-7.67 (m, 58H, C$_6$H$_5$— and C$_6$H$_4$—OMe)<br>$^{13}$C NMR (CDCl$_3$, δ, ppm): 54.94, 113.55, 122.7, 125.72, 126.89, 127.42 (t, J = 12.2 Hz), 127.8, 128.37, 128.47, 130.18, 130.38, 130.64, 131.79, 134.09 (d, J = 15 Hz), 135.79, 137.5, 147.87, 161.23<br>$^{29}$Si NMR (CDCl$_3$, δ, ppm): −49.04 (cis, trans), −83.26 (cis, trans), −84.55 (cis), −84.65 (trans), −84.74 (cis)<br>HRMS (FD): calcd. for C$_{78}$H$_{68}$O$_{16}$Si$_{10}$Na: 1563.2098; found: 1563.2080 |

Example XII

| | |
|---|---|
| Name of compound | trans-di [9,19-(E)-4-bromostyryl-4-methoxyphenyl] -1,3,5,7,11,13,15,17 octa(phenyl)pentacyclo [11.7.1.1$^{3,11}$.1$^{5,17}$.1$^{7,15}$] decasiloxane |
| Formula of compound | 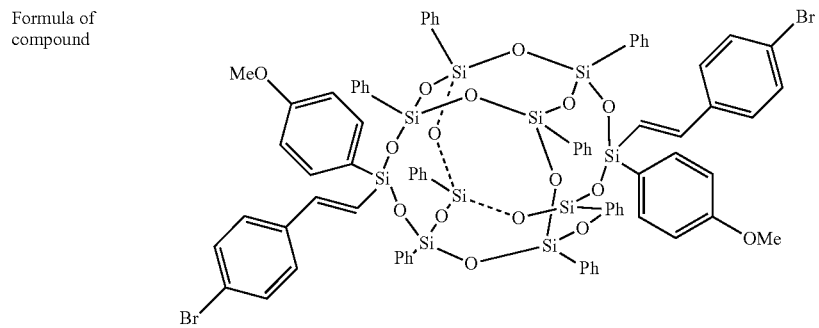 |
| Results of NMR + HRMS analyses | $^1$H NMR (CDCl$_3$, δ, ppm): 3.78-3.79 (overlapping s, 6H, OCH$_3$, cis and trans mixture), 6.52 (d, 2H, $J_{HH}$ = 19.2 Hz, =CH—Si), 7.29 (d, 2H, $J_{HH}$ = 19.2 Hz, =CH—C$_6$H$_4$—Br), 6.8-7.65 (m, 56H, C$_6$H$_5$—, C$_6$H$_4$—Br and C$_6$H$_4$—OMe)<br>$^{13}$C NMR (CDCl$_3$, δ, ppm): 54.96, 113.61, 122.39 (d, J = 3.2 Hz), 123.82 (d, J = 2.6 Hz), 125.37 (d, J = 1.9 Hz), 127.47 (t, J = 14.8 Hz), 127.84, 128.34, 130.31, 130.47, 131.46 (d, J = 1.9 Hz), 131.66, 134, 134.10, 134.12, 135.75 (d, J = 1.0 Hz), 136.41, 146.40, 161.33<br>$^{29}$Si NMR (CDCl$_3$, δ, ppm): −44.14 (cis, trans), −78.02 (cis, trans), −79.49 (br s, cis, trans)<br>HRMS (FD): calcd. for C$_{78}$H$_{66}$Br$_2$O$_{16}$Si$_{10}$Na: 1719.0308; found: 1719.0302 |

Example XIII

| | |
|---|---|
| Name of compound | trans-di[9,19-(E)-4-chlorostyryl-4-methoxyphenyl]-1,3,5,7,11,13,15,17 octa(phenyl)pentacyclo [11.7.1.1$_{3,11}$.1$_{5,17}$.1$_{7,15}$] decasiloxane |
| Formula of compound | 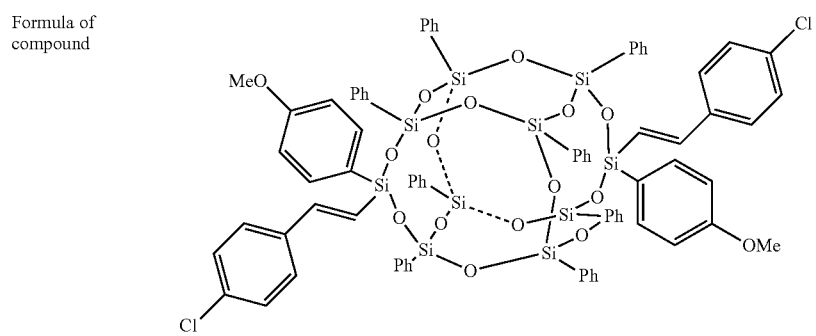 |
| Results of NMR + HRMS analyses | $^1$H NMR (CDCl$_3$, δ, ppm): 3.77-3.78 (overlapping s, 6H, OCH$_3$, cis and trans mixture), 6.50 (d, 2H, $J_{HH}$ = 19.2 Hz, =CH—Si), 7.13 (d, 2H, $J_{HH}$ = 19.2 Hz, =CH—C$_6$H$_4$—Cl), 6.79-7.63 (m, 56H, C$_6$H$_5$—, C$_6$H$_4$—Cl and C$_6$H$_4$—OMe)<br>$^{13}$C NMR (CDCl$_3$, δ, ppm): 54.97, 113.61, 123.63 (d, J = 2.3 Hz), 125.41 (d, J = 1.6 Hz), 127.46 (t, J =14.2 Hz), 127.84, 128.06, 128.51 (d, J = 1.7 Hz), 130.3, 130.46, 130.58, 131.67, 134.01, 134.12 (d, J = 2.0 Hz), 135.76 (d, J = 1.0 Hz), 135.99, 146.35, 161.32 (d, J = 1.1 Hz)<br>$^{29}$Si NMR (CDCl$_3$, δ, ppm): −49.34 (cis, trans), −83.24 (cis, trans), −84.71 (br s, cis, trans)<br>HRMS (FD): calcd. for C$_{78}$H$_{66}$Cl$_2$O$_{16}$Si$_{10}$Na: 1631.1319; found: 1631.1334 |

The invention claimed is:

1. A functionalized unsaturated double-decker divinylsilsesquioxane of the general formula 1,

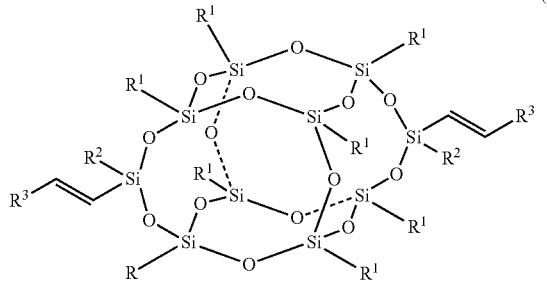

(1)

in which $R^1$ are the same and stand for an aryl group containing from 1 to 2 rings, $R^2$ are the same and stand for:
- Alkyl group containing carbon atoms from $C_1$ to $C_2$,
- Unsubstituted aryl group containing from 1 to 2 rings, or
- Monosubstituted aryl group containing from 1 to 2 rings and substituted at any site of the ring with an alkoxyl group comprising an alkyl group with carbon atoms from $C_1$ to $C_3$, $R^3$ are the same and stand for
- Group of formula 2

$$-R^4-R^5-\qquad(2)$$

where $R^4$ stands for an alkyl group containing carbon atoms from $C_1$ to $C_3$, and $R^5$ stands for an aryl group containing from 1 to 2 rings, Unsubstituted aryl group containing from 1 to 2 rings, or Aryl group containing from 1 to 2 rings and substituted at any site with:
- An alkyl group containing carbon atoms from $C_1$ to $C_2$,
- An alkoxyl group comprising an alkyl group containing carbon atoms from $C_1$ to $C_2$,
- halogen that is F, Cl, or Br, or
- fully substituted halogenalkyl containing carbon atoms from $C_1$ to $C_2$ and F or Cl.

* * * * *